United States Patent [19]

Beschke et al.

[11] 4,175,195
[45] Nov. 20, 1979

[54] PROCESS FOR THE PRODUCTION OF SUBSTITUTED PYRIDINE (A)

[75] Inventors: Helmut Beschke; Heinz Friedrich; Heribert Offermanns, all of Hanau, Fed. Rep. of Germany

[73] Assignee: Deutsche Gold- und Silber-Scheideanstalt vormals Roessler, Frankfurt, Fed. Rep. of Germany

[21] Appl. No.: 830,984

[22] Filed: Sep. 6, 1977

[30] Foreign Application Priority Data

Sep. 3, 1976 [DE] Fed. Rep. of Germany ....... 2639701

[51] Int. Cl.² .......................................... C07D 213/12
[52] U.S. Cl. ...................................... 546/250; 544/35; 544/333; 544/336; 546/167; 546/251; 546/257; 546/273; 546/275; 546/276; 546/281; 546/283; 546/284; 546/285

[58] Field of Search ......... 260/290 P, 296 D, 294.8 D; 544/333, 336, 35; 546/250, 251, 257, 273, 275, 276, 281, 283, 284, 285, 167

[56] References Cited

U.S. PATENT DOCUMENTS

| | | | |
|---|---|---|---|
| 2,877,228 | 3/1959 | Mahan | 260/290 P |
| 2,926,074 | 2/1960 | Berger | 260/290 P |
| 3,898,177 | 8/1975 | Beschke et al. | 260/290 R |
| 3,917,542 | 11/1975 | Beschke et al. | 260/290 P |
| 3,960,766 | 6/1976 | Beschke et al. | 260/290 R |

*Primary Examiner*—Alan L. Rotman
*Attorney, Agent, or Firm*—Cushman, Darby & Cushman

[57] ABSTRACT

Pyridines substituted in the 2-position by an aromatic or heteroaromatic group are prepared by reacting an aliphatic aromatic or aliphatic heteroaromatic ketone with an aliphatic oxo compound having a carbon to carbon ethylenic double bond on the carbon atom adjacent to the oxo group and ammonia in the presence of a dehydrating and dehydrogenating catalyst at a temperature of about 250° to 550° C.

20 Claims, 1 Drawing Figure

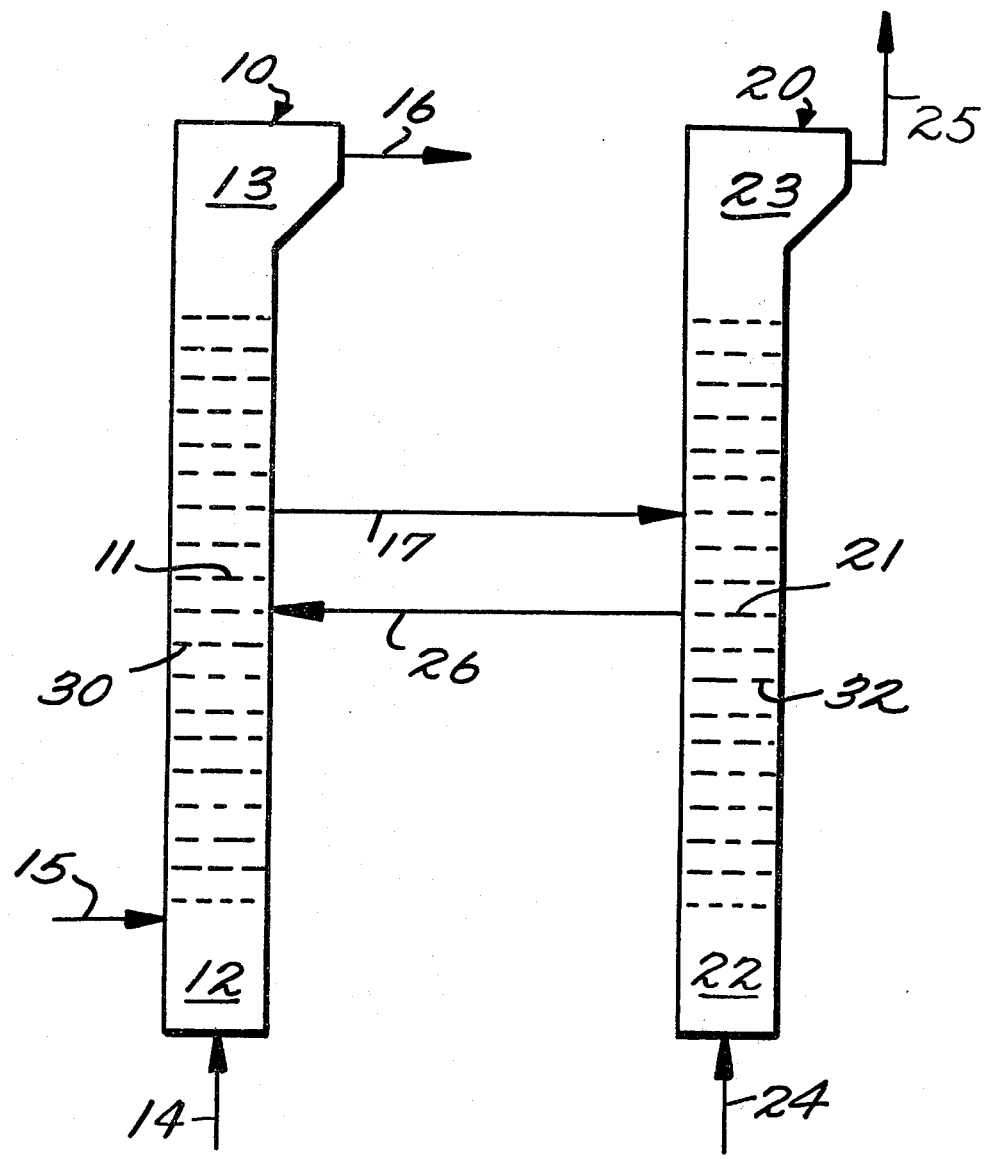

PROCESS FOR THE PRODUCTION OF SUBSTITUTED PYRIDINE (A)

BACKGROUND OF THE INVENTION

The invention is directed to a process for the production of pyridines substituted in the 2-position by an aromatic or heteroaromatic group. These substituted pyridines are important intermediate products for the production of medicines, plant protective agents and synthetic resins. For example 2,2'-dipyridyl is used to produce the known herbicide 1,1'-ethylene-2,2'-dipyridilium dibromide.

It is known to form 2-phenyl pyridine in addition to 4-phenyl pyridine by the action of benzene diazonium chloride on pyridine (Berichte Vol. 26, (1893) pages 2003 to 2004). 2-Phenyl pyridine is also produced by the reaction of phenyl lithium with pyridine (Organic Synthesis Vol. 18 (1938) pages 70 to 71) or by the addition of butadiene to vinyl pyridine and dehydrogenation of the 2-cyclohexene pyridine formed (J. Amer. Chem. Soc. Vol. 75 (1953) pages 4738 to 4740). Also, it is known to produce 2,2'-dipyridyl by reduction of pyridin-1-oxide with sodium in liquid ammonia (Chem. Abst. Vol. 49 (1955) 15895f) or by heating 2-bromopyridine with copper powder (Angew. Chem. Vol. 46 (1933) pages 21 to 22 or by heating pyridine with Raney-nickel (Organic Synthesis Vol. 46 (1966) pages 5 to 10).

These processes are little suited for use in producing the substituted pyridines on an industrial scale. They are expensive and cumbersome to handle. The yields are moderate. Besides in several cases, the starting materials are only difficulty accessible.

SUMMARY OF THE INVENTION

There has now been found a process for the production of pyridines substituted in the 2-position by an aromatic or heteroaromatic group by the catalytic reaction of an aliphatic aromatic ketone or aliphatic heteroaromatic ketone with an aliphatic oxo compound which has an ethylenically unsaturated carbon to carbon double bond on the carbon atom adjacent to the oxo group in the gas phase and with ammonia and in the presence of a dehydrating and dehydrogenating catalyst at a temperature of about 250° to 550° C. In this process a pyridine substituted in the 2-position by an aromatic or heteroaromatic group is produced from simple, easily accessible substances. High yields are produced. The process in contrast to the known processes is distinguished by being suited for use on an industrial scale.

According to the invention (1) an aliphatic-aromatic or aliphatic-heteroaromatic ketone of the general formula

in which $R_4$ is hydrogen or a straight or branched aliphatic chain, preferably an alkyl group with 1 to 12, especially 1 to 4 carbon atoms and $R_5$ is an aromatic or heteroaromatic ring, in a given case with one or more halogen, e.g., chlorine, bromine or fluorine, alkoxy, alkyl, hydroxy, morpholino or cyano group substituents is reacted (2) with an oxo compound of the general formula

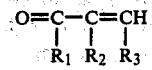

in which $R_1$, $R_2$ and $R_3$ are the same or different and are hydrogen or lower alkyl groups with preferably 1 to 6, especially 1 to 2, carbon atoms and in which in a given case the alkyl groups can be branched, and (3) with ammonia to form a compound of the general formula

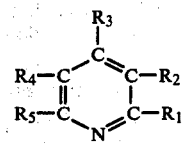

in which $R_1$, $R_2$, $R_3$, $R_4$ and $R_5$ are as defined above.

As aliphatic-aromatic or aliphatic-heteroaromatic ketones (I) there can be used for example 4-methyl acetophenone, 3-methyl acetophenone, 4-ethyl acetophenone, 2,4-dimethyl acetophenone, 4-butyl acetophenone, 4-sec.butyl acetophenone, 4-chloro acetophenone, 2,4-dichloro acetophenone, 4-bromo acetophenone, 4-fluoro acetophenone, 2-methyl-4-chloro acetophenone, 2-acetyl pyrane, valerophenone, caprophenone, laurophenone, myristophenone, 4-cyano acetophenone, 3-methoxy acetophenone, 3,4-dimethoxy acetophenone, 4-ethoxy acetophenone, 3-butoxy acetophenone, 4-morpholino acetophenone, acetovanillone, acetyl azulene, acetyl phenthiazine, acetyl triazole, acetyl anthracene, 2-acetyl naphthalene, 2-methyl-3-acetyl thiophene, 5-methyl-3-acetyl furane, preferably 3-acetyl thiophene, 1-acetyl naphthalene, 3-acetyl furane, 2-acetyl quinoline, acetyl quinolines with the acetyl group in the 3, 4, 5, 6 or 7-position, acetyl thiazole, e.g., 2-acetyl thiazole and 4-acetyl thiazole, acetyl toluene, e.g., 4-methyl acetophenone and 3-methyl acetophenone, acetyl indole, e.g., 2-acetyl indole, acetyl indene, e.g., 1-acetyl indene and 2-acetyl indene, acetyl N-methyl pyrrole, e.g., 3-acetyl N-methyl pyrrole and 2-acetyl N-methyl pyrrole, acetyl pyrimidine, e.g., 4-acetyl pyrimidine, acetyl thiopyrane, e.g., 2-acetyl thiopyrane, acetyl oxazole, e.g., 2-acetyl oxazole, acetyl pyrazine, e.g., 2-acetyl pyrazine, n-butyrophenone, n-valerophenone, isobutyrophenone and particularly acetophenone, propiophenone, 2-acetyl pyridine, 3-acetyl pyridine, 4-acetyl pyridine, 2-acetyl thiophene, 2-acetyl naphthalene and acetyl furane, e.g., 2-acetyl furane.

Suitable oxo compounds are for example, methacrolein, methyl crotyl ketone, crotonaldehyde, methyl vinyl ketone, ethyl vinyl ketone, 3-penten-2-one, hexyl vinyl ketone, heptyl vinyl ketone, 3-octene-2-one, and especially acrolein.

The reaction conditions such as temperature and pressure and the proportions of the reacting substances and the residence time in a given case to a certain extent are dependent upon each other according to the type of reacting substances and the type of catalyst.

In general, the reaction is carried out at a temperature between 250° and 550° C. In most cases there are preferred temperatures between 300° and 500° C., especially between 350° and 450° C. It is advantageous to work at pressures of about 1 to 4 bar. However, there can also be used lower or higher pressures although it is suitable not to substantially deviate from this pressure range since it permits the use of simple apparatus.

The proportions of ketone (I) to oxo compound (II) can be selected substantially at random, both stoichiometric as well as under or over stoichiometric being usable. Generally, it is advantageous to add about 0.5 to 10 moles of oxo compound per mole of ketone (I). Preferably there are used about 1 to 5 moles, especially 2 to 4 moles of oxo compound (II) per mole of ketone (I).

The ammonia can be present in the reaction in substantially any proportions from under stoichiometric to over stoichiometric. In most cases it is suitable to have present at least 0.5 mole of ammonia per mole of ketone (I), however, there can be as much as about 100 moles of ammonia per mole of ketone (I). Advantageously, there are employed about 1 to 20 moles of ammonia, preferably 2 to 15 moles of ammonia, especially 3 to 12 moles of ammonia, per mole of ketone (I).

The reaction takes place in the gas phase. It can be expedient to dilute the gases of ketone (I), oxo compound (II) and ammonia with inert gases. As inert gases there can be employed, for example, steam, air and especially nitrogen. Generally, it is expedient to use in all not more than about 20 moles of inert gas per mole of ketone (I). Preferably, there are used about 0.5 to 10 moles, particularly 1 to 5 moles of inert gas per mole of ketone (I).

As catalysts there can be employed those which have a dehydrating and dehydrogenating action. For example, these include the catalysts described in Hydrocarbon Processing, Vol. 47 (1968) pages 103 to 107 which are aluminum compounds such as aluminum oxide and aluminum silicate, optionally with addition of other metal oxides and fluorides. The entire disclosure of the Hydrocarbon Processing article is hereby incorporated by reference and relied upon.

With advantage there is used in the process catalysts produced according to German Offenlegungsschrift 2 151 417 and related Beschke U.S. Pat. No. 3,898,177; according to German OS 2 224 160 and related Beschke U.S. Pat. No. 3,960,766; and according to German OS 2 239 801 and related Beschke U.S. Pat. No. 3,917,542. The entire disclosure of Beschke U.S. Pat. Nos. 3,898,177; 3,917,542 and 3,960,766 are hereby incorporated by reference and relied upon.

These catalysts are prepared by treating with oxygen at temperatures of 550° to 1200° C. compounds of the elements Al, F and O which compounds also contain at least one element of the second, third or fourth groups of the periodic system (German Offenlegungsschrift 2 151 417 and related Beschke U.S. Pat. No. 3,898,177) or at least two elements of the second, fourth, fifth or sixth groups of the periodic system (German Offenlegungsschrift 2 224 160 and related Beschke U.S. Pat. No. 3,960,766) or at least one element of the second main group of the periodic system (German Offenlegungsschrift 2 239 801 and related Beschke U.S. Pat. No. 3,971,542). The catalysts are used in a fixed bed or preferably in a fluidized bed.

Beschke U.S. Pat. No. 3,898,177 describes the catalyst in claim 1 as consisting essentially of oxygen containing compounds of Al, F, at least one of the elements B and Si and at least one element from the second and fourth groups of the periodic system selected from the group consisting of Mg, Ba, Zn, Sn and Zr, said catalyst having been prepared by heating in the presence of oxygen at a temperature of 600° to 800° C.:

1. aluminum, aluminum oxide or an aluminum compound convertible to the oxide at said temperature;

2. a compound of fluorine, said fluorine having been added as ammonium fluoride, ammonium hydrogen fluoride, hydrogen fluoride, fluoboric acid, fluosilicic acid, boron trifluoride, magnesium fluoborate, magnesium fluosilicate, zinc fluosilicate or barium fluosilicate;

3. boron, silicon, boric oxide, silica or a compound of boron or silica convertible to the oxide at said temperature; and, 4. magnesium, zinc, tin, zirconium, magnesium oxide, zinc oxide, tin oxide or a compound of zirconium or barium convertible to the oxide at said temperature, the atomic ratio of Al to F being from 1000:25 to 1000:800 and the atomic ratio of Al to the total of (3) and (4) being from 1000:5 to 1000:20, the atomic ratio of the total of boron and silicon to the other element from the second and fourth groups being between 1 to 10 and 10 to 1.

Beschke U.S. Pat. No. 3,917,542 in claim 1 describes the catalyst as having been prepared by heating at 600° to 800° C. In the presence of gaseous oxygen, (1) aluminum metal, aluminum oxide or a compound of aluminum convertible to the oxide upon heating with gaseous oxygen at 600° to 800° C., (2) ammonium fluoride, hydrogen fluoride or a fluoride of an element of the second main group of the periodic system and (3) at least one element of the second main group of the periodic system, the oxide of said element or a compound of said element convertible to the oxide in the presence of gaseous oxygen at a temperature of 600° to 800° C., said catalyst consisting essentially of the elements Al, F, O and the element of the second main group of the periodic system.

Beschke U.S. Pat. No. 3,960,766 in claim 1 describes the catalyst as consisting essentially of the product obtained by treating with oxygen at a temperature of 550° to 1200° C. compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb and S, the ratios of the elements being Al to F of between 1000 to 10 and 1000 to 800 and of Al to the elements of the second, fourth, fifth and sixth groups being between 1000 to 5 and 1000 to 2000.

Especially advantageous is a procedure using the apparatus and method of German OS 2 449 340 and related Beschke U.S. application 622,488 filed Oct. 15, 1975 in which instead of the reactants mentioned in the German OS and Beschke ketone (I) and oxo compound (II) are fed into the reactor separate from the ammonia. Generally, the residence time in the reactor is between 0.2 and 5.0 seconds. The entire disclosure of the Beschke U.S. application 622,488 is hereby incorporated by reference and relied upon.

The working up of the gas mixture resulting from the reaction can take place in customary manner by washing the gases with a liquid, especially water or methanol and by further separation by means of extraction and distillation. With especially advantage there is employed the procedure of German OS 2 554 946 and related Beschke U.S. application 748,041 filed Dec. 6, 1976 in which the gas mixture is not washed but cooled and as a result partially condensed in such manner that any possible excess ammonia remains in the residual gas and with this is directly recycled.

BRIEF DESCRIPTION OF THE DRAWINGS

The single FIGURE of the drawing is a schematic illustration of an apparatus suitable for carrying out the invention.

Referring more specifically to the drawing, there is used a tubular reactor 10 provided with cooling and heating devices (not shown). The reactor suitably contains in the middle portion 11 gas distribution plates 30, but in the lower part 12 and the upper part 13 there is free space. The first reaction gas is led into the reactor from below through line 14 and so regulated that the catalyst in the reactor forms a fluidized bed. The other reactant gases are led through line 15 into the fluidized bed. The reaction mixture is drawn off from the reactor in the upper part thereof through the line 16. A portion of the catalyst is always transported via line 17 from the reactor 10 to a regenerator 20. This regenerator also is advantageously constructed similar to the reactor 10. The regenerator also suitably contains gas distribution plates 32 in the middle portion but there is free space in the lower portion 22 and in the upper portion 23. The oxygen or oxygen containing gas is led into the regenerator 20 from below through line 24. The gas flow is so regulated that the catalyst present in the regenerator forms a fluidized bed. The gas escaping from the regenerator via line 25 is discarded. A portion of the catalyst is continuously relieved from the regenerator 20 via line 26 into the reactor 10.

Unless otherwise indicated all parts and percentages are by weight.

The process can comprise, consist essentially of or consist of the steps set forth and the materials can comprise, consist essentially of or consist of those set forth.

DESCRIPTION OF THE PREFERRED EMBODIMENTS

EXAMPLE 1

There was used the apparatus of the drawing (also disclosed in German OS No. 2 449 340 and Beschke U.S. application No. 622,488). Reactor 10 and regenerator 20 consisted of tubes 70 mm wide which had in their lower portions a free space 12 or 22 which was 200 mm high; thereover at intervals of 50 mm there were provided 40 wire screens with meshes of 5 mm (30 and 32) each in the spaces 11 and 21. There were provided above free spaces 13 and 23 having a height of 600 mm and a width of up to 160 mm.

There were led into the reactor 10 in gaseous form in uniform flow hourly from below via line 14 a gas mixture of 1500 normal liters (i.e., measured at standard pressure and temperature) of nitrogen and 2150 normal liters of ammonia. In a vaporizer there was prepared hourly a gas mixture from 1350 grams of acrolein and 325 normal liters of nitrogen. In a further vaporizer there was prepared a similar gaseous mixture from 2880 grams of acetophenone and 325 normal liters of nitrogen. These gaseous mixtures were combined and from the side via line 15 were led into the fluidized layer 130 mm above the bottom of the reactor at a temperature of 250° C.

The reactor contained 2.0 kg of catalyst which was produced according to Beschke U.S. Pat. No. 3,960,766 Example 1a (and German Offenlegungsschrift 2 224 160) from aluminum oxide, magnesium nitrate and titanium tetrafluoride and had an atomic ratio of aluminum to magnesium to titanium to fluorine of 1000:25:25:100. The catalyst had a particle size between 0.4 and 1.0 mm.

The temperature in the reactor was held at 440° C. The reaction mixture leaving via line 16 was led at a temperature of 250° C. into a gas washing apparatus in which the phenyl pyridine and the pyridine and 3-methyl pyridine byproducts as well as unreacted acetophenone were washed out by means of methanol. The remaining residual gas of ammonia and nitrogen was recycled into the reactor.

The regenerator 20 contained an additional 2.0 kg of the catalyst. There were introduced into the regenerator from below via line 24 hourly 3000 normal liters of air. The temperature in the regenerator was held at 440° C. In a steady stream there were transferred hourly from the reactor to the regenerator 1.4 kg of catalyst and likewise there were returned 1.4 kg of catalyst from the regenerator to the reactor.

The acetophenone reaction was 80%. There were recovered hourly 1255 grams of 2-phenyl pyridine, 95 grams of pyridine and 264 grams of 3-methyl pyridine as well as 576 grams of unreacted acetophenone. This corresponds to a yield of 2-phenyl pyridine of 42% based on the reacted acetopheone as well as 10% of pyridine and 24% of 3-methyl pyridine based on the acrolein added. The 2-phenyl pyridine had a boiling point of 136° to 145° C. at 17 mbar. Its hydrochloride had a melting point of 118° C.

In the following examples there was used the same procedure as in Example 1.

EXAMPLE 2

| | |
|---|---|
| Starting Materials: | 2-acetyl pyridine, acrolein and ammonia in the molar ratios of 1:2:6 |
| Catalyst: | As in Example 1 |
| Reaction Temperature: | 440° C. |
| Reaction: | 100% of the 2-acetyl pyridine |
| Product: | 2,2'-dipyridyl, B.P. 135° C. at 17 mbar, M.P. 69.5° C. |
| Yield: | 69% based on the reacted 2-acetyl pyridine |
| Byproducts: | 8% pyridine and 21% 3-methyl pyridine based on the acrolein added |

EXAMPLE 3

| | |
|---|---|
| Starting Materials: | propiophenone, acrolein and ammonia in the molar ratios of 1:1:4 |
| Catalyst: | As in Example 1 |
| Reaction Temperature: | 440° C. |
| Reaction: | 89% propiophenone |
| Product: | 2-phenyl-3-methyl pyridine, B.P. 147° to 149° C. at 17 mbar, M.P. of hydrochloride 180° C. |
| Yield: | 58% based on the reacted propiophenone |
| Byproducts: | 13% pyridine and 23% 3-methyl pyridine based on the acrolein added |

EXAMPLE 4

| | |
|---|---|
| Starting materials: | 2-acetyl thiophene, acrolein and ammonia in the molar ratios of 1:2.5:10 |
| Catalyst: | As in Example 1 |
| Reaction Temperature: | 420° C. |
| Reaction: | 96% of the 2-acetyl thiophene |

-continued

| | |
|---|---|
| Product: | 2,2'-thienyl pyridine, B.P. 146° to 150° C. at 16 mbar, M.P. of the hydrochloride 140° C. |
| Yield: | 78% based on the reacted 2-acetyl thiophene |
| Byproducts: | 20% pyridine and 41% 3-methyl pyridine based on the acrolein added |

EXAMPLE 5

| | |
|---|---|
| Starting Materials | 2-acetyl naphthalene, acrolein and ammonia in the molar ratios of 1:3:12 |
| Catalyst: | As in Example 1 |
| Reaction Temperature: | 430° C. |
| Reaction: | 100% of the 2-acetyl naphthalene |
| Product: | 2,2'-naphthyl pyridine, B.P. 186° C. at 5 mbar, M.P. of the hydrochloride 187° C. |
| Yield: | 71% based on the reacted 2-acetyl naphthalene |
| Byproducts: | 16% pyridine and 35% 3-methyl pyridine based on the acrolein added |

EXAMPLE 6

| | |
|---|---|
| Starting Materials: | 2-acetyl furane, acrolein and ammonia in the molar ratios of 1:2.8:11.2 |
| Catalyst: | As in Example 1 |
| Reaction Temperature: | 440° C. |
| Reacton: | 93% of the 2-acetyl furane |
| Product: | 2,2'-furyl pyridine, B.P. 111° to 116° C. at 17 mbar |
| Yield: | 53% based on the reacted 2-acetyl furane |
| Byproducts: | 18% pyridine and 39% methyl pyridine based on the acrolein added |

EXAMPLE 7

| | |
|---|---|
| Starting Materials: | 3-acetyl pyridine, acrolein and ammonia in the molar ratios of 1:2.6:10.4 |
| Catalyst: | As in Example 1 |
| Reaction Temperature: | 420° C. |
| Reaction: | 98% of the 3-acetyl pyridine |
| Product: | 2,3'-dipyridyl, B.P. 109° to 113° C. at 1 mbar |
| Yield: | 57% based on the reacted 3-acetyl pyridine |
| Byproducts: | 16% pyridine and 37% 3-methyl pyridine based on the acrolein added |

EXAMPLE 8

| | |
|---|---|
| Starting Materials: | 4-acetyl pyridine, acrolein and ammonia in the molar ratios of 1:2.5:10 |
| Catalyst: | As in Example 1 |
| Reaction Temperature: | 410° C. |
| Reaction: | 98% of the 4-acetyl pyridine |
| Product: | 2,4'-dipyridyl, B.P. 110° to 114° C. at 1 mbar |
| Yield: | 56% based on the reacted 4-acetyl pyridine |
| Byproducts: | 16% pyridine and 36% 3-methyl pyridine based on the acrolein added |

EXAMPLE 9

| | |
|---|---|
| Starting Materials: | acetophenone, acrolein and ammonia in the molar ratios of 1:2.7:10.8 |
| Catalyst: | According to Beschke U.S. Pat. No. 3,898,177 Example 5 (and German OS 2 151 417) from aluminum oxide, magnesium nitrate and fluosilicic acid, atomic ratio aluminum to magnesium to silicon to fluorine of 1000:24:26:156 |
| Reaction Temperature: | 370° C. |
| Reaction: | 97% of the acetophenone |
| Product: | 2-phenyl pyridine, B.P. 136° to 145° C. at 17 mbar, M.P. of the hydrochloride 118° C. |
| Yield: | 43% based on the reacted acetophenone |
| Byproducts: | 13% pyridine and 26% 3-methyl pyridine based on the acrolein added |

EXAMPLE 10

| | |
|---|---|
| Starting Materials: | acetophenone, acrolein and ammonia in the molar ratios of 1:3:12 |
| Catalyst: | According to Beschke U.S. Pat. No. 3,917,542 Example 1 (and German OS 2 239 801) from aluminum oxide, magnesium nitrate and ammonium hydrogen fluoride in the atomic ratio aluminum to magnesium to fluorine of 1000:25:50 |
| Reaction Temperature: | 400° C. |
| Reaction: | 93% of the acetophenone |
| Product: | 2-phenyl pyridine, B.P. 136° to 145° C. at 17 mbar, M.P. of the hydrochloride 118° C. |
| Yield: | 48% based on the reacted acetophenone |
| Byproducts: | 12% pyridine and 27% 3-methyl pyridine based on the acrolein added |

EXAMPLE 11

| | |
|---|---|
| Starting Materials: | 2-acetyl thiophene, crotonaldehyde and ammonia in the molar ratios of 1:2.4:12 |
| Catalyst: | As in Example 1 |
| Reaction Temperature: | 420° C. |
| Reaction: | 92% of the 2-acetyl thiophene |
| Product: | 2-(2'-thienyl)-4-methyl pyridine, B.P. 125° to 134° C. at 3 mbar |
| Yield | 39% based on the reacted 2-acetyl thiophene |
| Byproducts: | 18% pyridine, 14% 2-methyl pyridine and 32% 4-methyl pyridine based on the crotonaldehyde added |

EXAMPLE 12

| | |
|---|---|
| Starting Materials: | 2-acetyl thiophene, methacrolein and ammonia in the molar ratios of 1:2.2:11 |
| Catalyst: | As in Example 1 |

-continued

| | |
|---|---|
| Reaction Temperature: | 410° C. |
| Reaction: | 93% of the 2-acetyl thiophene |
| Product: | 2-(2'-thienyl)-5-methyl pyridine, B.P. 122° to 135° C. at 5 mbar |
| Yield: | 44% based on the reacted 2-acetyl thiophene |
| Byproducts: | 47% pyridine and 29% 3,5-dimethyl pyridine based on the methacrolein added |

EXAMPLE 13

| | |
|---|---|
| Starting Materials: | 2-acetyl thiophene, methyl vinyl ketone and ammonia in the molar ratios of 1:2.3:11.5 |
| Catalyst: | As in Example 1 |
| Reaction Temperature: | 400° C. |
| Reaction: | 100% of the 2-acetyl thiophene |
| Product: | 2-(2'-thienyl)-6-methyl pyridine, B.P. 138° to 145° C. at 10 mbar |
| Yield: | 79% based on the reacted 2-acetyl thiophene |
| Byproducts: | 26% collidine mixture based on the methyl vinyl ketone added |

EXAMPLE 14

| | |
|---|---|
| Starting Materials: | acetophenone, acrolein and ammonia in the molar ratios of 1:1:4 |
| Catalyst: | aluminum silicate consisting of 87% SiO$_2$ and 13% Al$_2$O$_3$, BET surface area 500 m$^2$/g, particle size 0.4 to 1.0 mm, pore volume 0.75 cm$^3$/g, pore diameter 60 angstroms |
| Reaction Temperature: | 420° C. |
| Reaction: | 86% of the acetophenone |
| Product: | 2-phenyl pyridine, B.P. 136° to 145° C. at 17 mbar, M.P. of the hydrochloride 118° C. |
| Yield: | 40% based on the reacted acetophenone |
| Byproducts: | 12% pyridine and 34% 3-methyl pyridine based on the acrolein added |

What is claimed is:

1. A process for the production of a pyridine having an aromatic or heteroaromatic substituent in the 2-position comprising catalytically reacting a aliphatic-aromatic or aliphatic-heteroaromatic ketone with an aliphatic oxo compound having a carbon to carbon ethylenic double bond on the carbon adjacent to the oxo group and ammonia in the gas phase at a temperature from about 250° to 550° C. in the presence of a dehydrating and dehydrogenating catalyst which is (1) a catalyst consisting essentially of oxygen containing compounds of Al, F. at least one of the elements B and Si and at least one element from the second and fourth groups of the periodic system selected from the group consisting of Mg, Ba, Zn, Sn, and Zr, said catalyst having been prepared by heating in the presence of oxygen at a temperature of 600° to 800° C.;
   1. aluminum, aluminum oxide or an aluminum compound convertible to the oxide at a said temperature,
   2. a compound of fluorine, said fluorine having been added as ammonium fluoride, ammonium hydrogen fluoride, hydrogen fluoride, fluoboric acid, fluosilicic acid, boron trifluoride, magnesium fluoborate, magnesium fluosilicate, zinc fluosilicate or barium fluosilicate,
   3. boron, silicon, boric oxide, silica or a compound of boron or silica convertible to the oxide at said temperature and
   4. magnesium, zinc, tin, zirconium, magnesium oxide, zinc oxide, tin oxide or a compound of zirconium or barium convertible to the oxide at said temperature, the atomic ratio of Al to F being from 1000:25 to 1000:800 and the atomic ratio of Al to the total of (3) and (4) being from 1000:5 to 1000:200, the atomic ratio of the total of boron and silicon to the other element from the second and fourth groups being between 1 to 10 and 10 to 1 or (2) a catalyst having been prepared by heating at 600° to 800° C. in the presence of gaseous oxygen (1) aluminum metal, aluminum oxide, or a compound of aluminum convertible to the oxide upon heating with gaseous oxygen at 600° to 800° C., (2) ammonium fluoride, hydrogen fluoride or a fluoride of an element of the second main group of the periodic system and (3) at least one element of the second main group of the periodic system, the oxide of said element or a compound of said element convertible to the oxide in the presence of gaseous oxygen at a temperature of 600° to 800° C., said catalyst consisting essentially of the elements Al, F, O and the element of the second main group of the periodic system or (3) a catalyst consisting essentially of the product obtained by treating with oxygen at a temperature of 550° to 1200° C. compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb and S, the ratios of the elements being Al to F of between 1,000 to 10 and 1,000 to 800 and of Al to the elements of the second, fourth, fifth and sixth groups being between 1,000 to 5 and 1,000 to 200.

2. The process of claim 1 wherein the catalyst is oxygen containing compounds of Al, F at least one of the elements B and Si and at least one element from the second and fourth groups of the periodic system selected from the group consisting of Mg, Ba, Zn Sn and Zr, said catalyst having been prepared by heating in the presence of oxygen at a temperature of 600° to 800° C.;
   1. aluminum, aluminum oxide or an aluminum compound convertible to the oxide at a said temperature,
   2. a compound of fluorine, said fluorine having been added as ammonium fluoride, ammonium hydrogen fluoride, hydrogen fluoride, fluoboric acid, fluosilicic acid, boron trifluoride, magnesium fluoborate, magnesium fluosilicate, zinc fluosilicate or barium fluosilicate,
   3. boron, silicon, boric oxide, silica or a compound of boron or silica convertible to the oxide at said temperature and
   4. magnesium, zinc, tin, zirconium, magnesium oxide, zinc oxide, tin oxide or a compound of zirconium or barium convertible to the oxide at said temperature, the atomic ratio of Al to F being from 1000:25 to 1000:80 and the atomic ratio of Al to the total of (3) and (4) being from 1000:5 to 1000:200, the atomic ratio of the total of boron and silicon to the other element from the second and fourth groups being between 1 to 10 and 10 to 1.

3. The process of claim 1 wherein the catalyst is a catalyst having been prepared by heating at 600° to 800° C. in the presence of gaseous oxygen (1) aluminum metal, aluminum oxide, or a compound of aluminum convertible to the oxide upon heating with gaseous oxygen at 600° to 800° C., (2) ammonium fluoride, hydrogen fluoride or a fluoride of an element of the second main group of the periodic system and (3) at least one element of the second main group of the periodic system, the oxide of said element or a compound of said element convertible to the oxide in the presence of gaseous oxygen at a temperature of 600° to 800° C., said catalyst consisting essentially of the elements Al, F, O and the element of the second main group of the periodic system.

4. The process of claim 1 wherein the catalyst is a catalyst consisting essentially of the product obtained by treating with oxygen at a temperature of 550° to 1200° C. compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb and S, the ratios of the elements being Al to F of between 1,000 to 10 and 1,000 to 800 and of Al to the elements of the second, fourth, fifth and sixth groups being between 1,000 to 5 and 1,000 to 200.

5. The process of claim 1 wherein the aliphatic-aromatic or aliphatic-heteroaromatic substituted pyridine has the formula

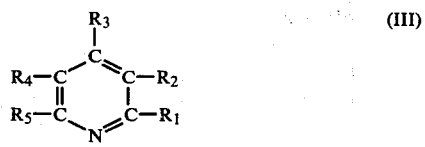

(III)

wherein $R_1$, $R_2$ and $R_3$ are hydrogen or lower alkyl, $R_4$ is hydrogen or alkyl having 1–12 carbon atoms and $R_5$ is an aromatic or heteroaromatic ring which is unsubstituted or substituted by halogen, alkoxy, alkyl, hydroxy, the aliphatic-aromatic or aliphatic-heteroaromatic ketone has the formula

(I)

and the oxo compound has the formula

(II)

6. The process of claim 5 wherein $R_4$ is hydrogen or alkyl with 1 to 12 carbon atoms, $R_5$ is substituted or unsubstituted phenyl, naphthyl, indenyl, anthracenyl, azulenyl or a heteroaromatic compound which has in the heterocyclic ring 5 to 6 atoms, the hetero atoms being one oxygen atom, one sulfur atom, one nitrogen atom, one nitrogen and one sulfur atom, one nitrogen and one oxygen atom or two nitrogen atoms.

7. The process of claim 5 wherein $R_4$ is hydrogen or alkyl of 1 to 6 carbon atoms and $R_1$, $R_2$ and $R_3$ are hydrogen or alkyl of 1 to 6 carbon atoms.

8. The process of claim 7 wherein $R_1$, $R_2$ and $R_3$ are hydrogen or alkyl of 1 to 2 carbon atoms and $R_5$ is unsubstituted or has 1 to 2 substituents which are halogen, lower alkoxy, lower alkyl, hydroxy or cyano.

9. The process of claim 8 wherein (II) is acrolein.

10. The process of claim 5 wherein (I) is methyl acetophenone, cyanoacetophenone, methoxyacetophenone, dimethoxyacetophenone, acetovanillone, acetylazulene, acetyl phenothiazine, acetyl triazole, acetyl anthracene, acetyl thiophene, acetyl naphthalene, acetyl furane, acetyl quinoline, acetyl toluene, acetyl thiazole, acetyl indole, acetyl indene, acetyl N-methyl pyrrole, acetyl pyrimidine, acetyl thiopyrane, acetyl oxazole, acetyl pyrazine, propiophenone, butyrophenone, valerophenone, acetyl pyridine, acetyl thiophene or acetyl furane and (II) is acrolein, methacrolein, crotonaldehyde, alkyl vinyl ketone having 1 to 2 carbon atoms in the alkyl group or 3-penten-2-one.

11. The process of claim 10 wherein (I) is acetophenone, 2-acetyl pyridine, propiophenone, 2-acetyl thiophene, 2-acetyl naphthalene, 2-acetyl furane, 3-acetyl pyridine or 4-acetyl pyridine and (II) is acrolein, methacrolein, crotonaldehyde or methyl vinyl ketone.

12. The process of claim 11 wherein (II) is acrolein.

13. The process of claim 10 wherein $R_5$ is unsubstituted ketone.

14. The process of claim 5 wherein the reaction temperature is 300° to 500° C.

15. The process of claim 14 wherein the reaction temperature is 350° to 450° C.

16. The process of claim 5 wherein there is used b 1 to 5 moles of oxo compound per mole of ketone (I).

17. The process of claim 16 wherein there is used 1 to 20 moles of ammonia per mole of ketone (I).

18. The process of claim 17 wherein the reaction is carried out in the presence of an inert gas.

19. The process of claim 18 comprising carrying out the reaction in a fluidized bed and the ketone (I) and oxo compound (II) are added together to the reaction zone separate from the ammonia.

20. The process of claim 5 wherein when $R_5$ is a heteroaromatic ring it is a heterocyclic ring of 5 to 6 carbon atoms, the hetero atoms being one oxygen atom, one sulfur atoms, one nitrogen atom, one nitrogen and one sulfur atom, one nitrogen and one oxygen atom or two nitrogen atoms.

* * * * *

UNITED STATES PATENT AND TRADEMARK OFFICE
CERTIFICATE OF CORRECTION

PATENT NO. : 4,175,195

DATED : November 20, 1979

INVENTOR(S) : BESCHKE, Helmut; FRIEDRICH, Heinz and OFFERMANNS, Heribert

It is certified that error appears in the above-identified patent and that said Letters Patent are hereby corrected as shown below:

Col. 3, line 57 change "3,971,542 to --3,917,542--.

Col. 4, line 15 change "1000:20" to --1000:200--.

Col. 10, line 64 change "1000:80" to --1000:800--.

*Signed and Sealed this*

*Twenty-fifth* Day of *March 1980*

[SEAL]

*Attest:*

SIDNEY A. DIAMOND

*Attesting Officer*        *Commissioner of Patents and Trademarks*